(12) United States Patent
Lau

(10) Patent No.: US 12,090,176 B2
(45) Date of Patent: Sep. 17, 2024

(54) USE OF EXTRACT FROM RABBIT SKIN INFLAMED BY VACCINIA VIRUS IN TREATING HEMATOPOIETIC SYSTEM DAMAGE

(71) Applicant: NEXUS BIO-DRUG DEVELOPMENT LIMITED, Hong Kong (CN)

(72) Inventor: Shing Hing Lau, Hong Kong (CN)

(73) Assignee: NEXUS BIO-DRUG DEVELOPMENT LIMITED, Hong Kong (CN)

( * ) Notice: Subject to any disclaimer, the term of this patent is extended or adjusted under 35 U.S.C. 154(b) by 449 days.

(21) Appl. No.: 17/604,040

(22) PCT Filed: Apr. 17, 2019

(86) PCT No.: PCT/CN2019/083027
§ 371 (c)(1),
(2) Date: Nov. 15, 2021

(87) PCT Pub. No.: WO2020/211009
PCT Pub. Date: Oct. 22, 2020

(65) Prior Publication Data
US 2022/0202873 A1      Jun. 30, 2022

(51) Int. Cl.
*A61K 35/36* (2015.01)
*A61P 7/00* (2006.01)

(52) U.S. Cl.
CPC ............... *A61K 35/36* (2013.01); *A61P 7/00* (2018.01)

(58) Field of Classification Search
CPC ..................................................... A61K 35/36
See application file for complete search history.

(56) References Cited

FOREIGN PATENT DOCUMENTS

| | | |
|---|---|---|
| CN | 1205233 A | 1/1999 |
| CN | 1055249 C | 8/2000 |
| CN | 1493302 A | 5/2004 |
| CN | 1613305 A | 5/2005 |
| CN | 101238116 A | 8/2008 |
| CN | 101732348 A | 6/2010 |
| CN | 109504649 A | 3/2019 |
| EP | 1557171 A | 7/2005 |
| JP | S55-87724 A | 7/1980 |
| JP | 2001058949 A | 3/2001 |

(Continued)

OTHER PUBLICATIONS

Gabrielyan et al., "Cerebral injuries caused by platelet and leukocyte activation and their correction with neurotropin," Experimental Biology and Medicine 112(10):391-393, 1991.*

(Continued)

*Primary Examiner* — Rosanne Kosson
(74) *Attorney, Agent, or Firm* — Michael Best & Friedrich LLP

(57) ABSTRACT

Disclosed is therapeutic use of an extract from rabbit skin inflamed by vaccinia virus. Particularly, disclosed is use of an extract from rabbit skin inflamed by vaccinia virus in treating hematopoietic system damage or pancytopenia induced by an anti-cancer therapy. Moreover, disclosed is use of an extract from rabbit skin inflamed by vaccinia virus in treating leukopenia induced by an anti-cancer therapy. Further, the extract from rabbit skin inflamed by vaccinia virus can be Lepalvir.

6 Claims, 1 Drawing Sheet

(56) References Cited

FOREIGN PATENT DOCUMENTS

| WO | 2004060381 A1 | 7/2004 |
|---|---|---|
| WO | 2010054531 A1 | 5/2010 |
| WO | 2016165102 A1 | 10/2016 |
| WO | 2020248240 A1 | 12/2020 |

OTHER PUBLICATIONS

T. Hata et al., "Changes in Platelet Count and Related Parameters in SART-Stressed Mice and the Action of Administered Neurotropin," Japan J. Pharmacol., vol. 47. No. 4., pp. 349-356 (8 pages)(Aug. 31, 1988).
International Search Report for corresponding International Application No. PCT/CN2019/083027, dated Mar. 3, 2020 (9 pages).
Chinese First Office Action for Related Application No. 201980095482. 4, dated Feb. 3, 2024 (13 pages, including translation).
European Patent Office Extended Search Report for Application No. 19924869.1 dated Nov. 7, 2022 (18 pages).
Mori et al., "Effect of a Non-Protein Fraction from an Extract of the Inflamed Skin of Rabbits Inoculated with Vaccina Virus Neurotropin on Meth A-Induced Delayed Type Hypersensitivity", Japan J. Pharmacol., 1990, vol. 54, pp. 468-472.
Hata et al., "Effect of neurotropin on SART stress (stress caused by alteration of rhythms in environmental temperature) in mice and rats", Medline, 1975, abstract, 1 page.
Gabrielian et al., "Cerebrovascular Injuries Induced by Activation of Platelets and Leukocytes in Vivo and Their Correction by Neurotropin", Japan J. Pharmacol., 1992, vol. 60, pp. 51-54.
Yoshiyama et al., "A Boy with Hemophilia and AIDS-Related Complex Treated with Neurotropin A Neuroimmunomodulator", ACTA Paediatricia Japonica, 2009, vol. 30, No. 3, pp. 319-321.
European Patent Office Extended Search Report for Application No. 19932445.0 dated Dec. 22, 2022 (11 pages).
Mizushima et al., "Antitumor Therapeutic Effect of Neurotropin on Transplanted Tumors in Rats", Oncology, vol. 41, 1984, pp. 289-292.
Tomiyama et al., "Antitumor activity of an extract neurotropin isolated from the inflamed skin of rabbits inoculated with vaccinia virus", Cancer and Chemotherapy, 1984, vol. 11, No. 10, abstract, 1 page.
Toge et al., "Enhancement of antitumor activity of Propionibacterium avidum in combined with neurotropin in tumor bearing mice", Cancer and Chemotherapy, 1983, vol. 10, No. 11, abstract, 1 page.
Japanese Patent Office Action for Related Application No. 2021-562049 dated Aug. 1, 2023 (9 pages, including English translation).
Lirong et al., "Radiation protection effect and its mechanism of multiple nilestriol administrations on the mice with bone marrow type of acute radiation syndrome", Chinese Journal of Radiological Medicine and Protection, 2016, Issue 6, pp. 412-418.
Qi et al., "Antitumor Activity of Extracts from Rabbit Skins Inflamed by Viccinia Virus Vaccine in vitro," International Journal of Pharmaceutical Research, 2018, vol. 45, No. 8, pp. 597-602.
Chen, et al., "Analgecine Enhances the Anti-tumor Response of Radiotherapy byincreasing Apoptosis and Cell Cycle Arrest in Non-Small Cell Lung Cancer," "Oncotarget, 2017, vol. 8, No. 46, pp. 80730-80740."
International Search Report and Written Opinion for Application No. PCT/CN2019/091337, dated Mar. 16, 2020.
Chinese Patent Office Action for Related Application No. 201980097494.0 dated Mar. 8, 2023 (9 pages, including an English statement of relevance).
Chen, et al., "Analgecine enhances the anti-tumor response of radiotherapy by increasing apoptosis and cell cycle arrest in non-small cell lung cancer," Impact Journals, Oncotarget, vol. 8, No. 46, 2017 (pp. 80730-80740).
Yue, et al., "Antitumor activity of extracts from rabbit skins inflamed by Viccinia virus vaccine in vitro," J Int Pharm Res, vol. 45, No. 8, Aug. 2018 (6 pages).
European Patent Office Action for Application No. 19924869.1 dated Feb. 9, 2024 (17 pages).
Shionogi & Co., Ltd., package insert for ENDOXAN for Injection 100mg/ENDOXAN for Injection 500mg, 17th Edition, Mar. 2019 (8 pages including statement of relevance).
Miki, T. et al., "A transition of chemotherapeutic and other agents for treatment of prostate cancer," Japanese Journal of Urological Surgery, 2013, 26(5), p. 799-802 (6 pages including statement of relevance).
Gabrielian, et al., "Cerebrovascular Injuries Induced by Activation of Platelets and Leukocytes in Vivo and Their Correction by Neurotropin," Japan J. Pharmacol., vol. 60, 1992 (p. 51-54).
Hata, et al., "Changes in Platelet Count and Related Parameters in SART-Stressed Mice eand the Action of Administered Neurotropin," Japan. J. Pharmacol., vol. 47, 1988, (p. 349-356).
Japanese Patent Office Action for Related Application No. 2021562049 dated Mar. 7, 2023 (4 pages, including an English statement of relevance).
Matsui, et al., Side effects and supportive care in lung cancer chemotherapyaHistory of Medicine, vol. 157, No. 9, 1991 (p. 555-558).
Mori, et al., "Effect of a Non-Protein Fraction from an Extract of the Inflamed Skin of Rabbits Inoculated with Vaccinia Virus (Neurotropin) on Meth A-Induced Delayed Type Hypersensitivity," Japan J. Pharmacol. vol. 54, 1990 (5 pages).
Takeuchi et al., "Effect of neurotropin on lymphocytes impaired by chemotherapy," Medicine and Biology, 1981 vol. 103, No. 6 (p. 565-569).
Tomitaro, et al., "Effects of SART on stress symptoms in mice and rats: The role of Neurotropin," Folia Pharmacol. Japon, vol. 71, 1975 (p. 211-220).
Yamaguchi, "Bone marrow suppression and hematological toxicity," Japanese Clinical One, 2014, vol. 72, No. 2, (p. 531-535).
Yanagihara Shinta Takao, "Immunopharmacological Actions of Neurotropin (Part 2)—Influence on Graft-versus-host reaction Yukiya," Folia Pharmacological Japonica (Folia Pharmacol. Japon.), 1981, vol. 78 (p. 451-458).
Japanese Patent Office Action for Related Application No. 2021-574202 dated Apr. 25, 2023 (9 pages, English translation included).

\* cited by examiner

USE OF EXTRACT FROM RABBIT SKIN INFLAMED BY VACCINIA VIRUS IN TREATING HEMATOPOIETIC SYSTEM DAMAGE

FIELD OF INVENTION

The invention relates to the field of medicine. Specifically, the present invention relates to new therapeutic use of extract from rabbit skin inflamed by vaccinia virus. More specifically, the present invention relates to use of the extract for the treatment of hematopoietic system damage or pancytopenia induced by anti-cancer therapy.

BACKGROUND ART

Early diagnosis and detection of cancer is possible through regular physical examinations, and there has been steady improvement in the rate of successful resection of primary cancers achieved through surgery. However, a variety of anti-cancer therapies (including anti-cancer radiotherapy or anti-cancer drug therapy) are still employed to treat advanced cancer or cancer with metastatic lesions. Anti-cancer therapy not only causes damages to cancer cells, but also to normal cells with active cell division, such as bone marrow hematopoietic cells. The side effects resulting from anti-cancer drugs include hematopoietic damage and bone marrow suppression. They are mainly manifested as a decrease in white blood cells, with varying degrees of decrease in red blood cells and platelets. When receiving anti-cancer therapy, the patient may not be able to produce enough white blood cells to resist invading bacteria and viruses, which can easily lead to life-threatening infections.

Under such circumstances, there is an urgent need to develop drugs for alleviating or treating hematopoietic damage and bone marrow suppression induced by anti-cancer therapy.

Nilestriol is known to be used to relieve hematopoietic system damage caused by anti-cancer radiotherapy (see Yi Lirong et al., *Chinese Journal of Radiological Medicine and Protection*, June 2016, Vol. 36, No. 6, page 412-417). However, there is still a need to develop other drugs to treat hematopoietic system damage caused by anti-cancer therapies, especially anti-cancer agents.

As used herein, "the extract from rabbit skin inflamed by vaccinia virus" refers to the active substances extracted from the rabbit skin inflamed by vaccinia virus, as described in Chinese patent NO. ZL98103220.6, the entirety of which is incorporated herein by reference. Such extract from rabbit skin inflamed by vaccinia virus are commercial available, with trade name of Lepalvir, which is manufactured by Vanworld Pharmaceutical (Rugao) Co. Ltd. The extract from rabbit skin inflamed by vaccinia virus and its pharmacological effects are also described in WO2010/054531, the entirety of which is incorporated herein by reference. However, before the filing of the present invention, it was not known whether the extract is effective for treating hematopoietic system damage or pancytopenia induced by anti-cancer therapy.

SUMMARY OF THE INVENTION

The objective of the present invention comprises the provision of agents for preventing, alleviating or treating hematopoietic system damage or pancytopenia induced by anti-cancer therapy. More specifically, the objective of the present invention comprises the provision of agents for preventing, alleviating or treating leukopenia induced by anti-cancer therapy.

The technical problem of the present invention is solved by providing extract from rabbit skin inflamed by vaccinia virus, preferably Lepalvir.

In general, the inventors found that extract from rabbit skin inflamed by vaccinia virus can effectively prevent, treat or alleviate the side effects induced by anti-cancer therapy. Specifically, the extract can effectively prevent, treat or alleviate hematopoietic system damage or bone marrow suppression induced by anti-cancer therapy. More specifically, the extract can effectively prevent, treat or alleviate leukopenia induced by anti-cancer therapy.

It is worth emphasizing that the leukopenia induced by anti-cancer therapy can be different from the leukopenia induced by other general drugs. For example, antibiotics (such as phorbol ester) may induce agglutination of platelets and white blood cells, or some anti-tuberculosis agents (such as isoniazid) may induce antibodies that bind to white blood cells in the body, which will cause the destruction or reduction of white blood cells in the bloodstream. However, these processes are aimed at the existing and generated white blood cells, which are relatively short-lived and do not involve damage to hematopoietic function or bone marrow suppression. In contrast, anti-cancer therapy not only kills tumor cells, but also kills other proliferating cells such as bone marrow hematopoietic cells. Therefore, the white blood cell reduction caused by anti-cancer drugs is significantly different from the white blood cell reduction caused by these drugs.

In addition, the inventors found that the extract from rabbit skin inflamed by vaccinia virus can effectively restore or increase the weight of a patient receiving anti-cancer therapy. The weight recovery or increase may be an indicator that the extract is effective in preventing or treating the above-mentioned diseases or disorders.

In one aspect, the present invention relates to the use of extract from rabbit skin inflamed by vaccinia virus in the preparation of a medicament for preventing or treating hematopoietic system damage induced by anti-cancer therapy in a patient. In one aspect, the present invention relates to extract from rabbit skin inflamed by vaccinia virus, for use in the prevention or treatment of hematopoietic system damage induced by anti-cancer therapy. In one aspect, the present invention relates to a method for preventing or treating hematopoietic system damage induced by anti-cancer therapy, the method comprising administering a therapeutically effective amount of extract from rabbit skin inflamed by vaccinia virus to a patient in need thereof. In this aspect, the hematopoietic system damage comprises bone marrow suppression. In this aspect, the hematopoietic system damage or bone marrow suppression is manifested as leukopenia.

In one aspect, the present invention relates to the use of extract from rabbit skin inflamed by vaccinia virus in the preparation of a medicament for preventing or treating bone marrow suppression induced by anti-cancer therapy in a patient. In one aspect, the present invention relates to extract from rabbit skin inflamed by vaccinia virus, for use in the prevention or treatment of bone marrow suppression induced by anti-cancer therapy. In one aspect, the present invention relates to a method for preventing or treating bone marrow suppression induced by anti-cancer therapy, the method comprising administering a therapeutically effective amount of extract from rabbit skin inflamed by vaccinia virus to a patient in need thereof. In the above aspects, the hematopoietic system damage or bone marrow suppression is manifested as leukopenia. In this aspect, bone marrow suppression is manifested as leukopenia.

In one aspect, the present invention relates to the use of extract from rabbit skin inflamed by vaccinia virus in the preparation of a medicament for restoring or improving the function of the hematopoietic system in a patient receiving anti-cancer therapy. In one aspect, the present invention relates to extract from rabbit skin inflamed by vaccinia virus for use in restoring or improving the function of the hematopoietic system in a patient receiving anti-cancer therapy. In one aspect, the present invention relates to a method for restoring or improving the function of the hematopoietic system in a patient receiving anti-cancer therapy, the method comprising administering a therapeutically effective amount of extract from rabbit skin inflamed by vaccinia virus to the patient receiving anti-cancer therapy. In this aspect, restoring or improving the function of the hematopoietic system comprises eliminating or reducing bone marrow suppression. In the aspect, restoring or improving the function of the hematopoietic system comprises increasing the number of white blood cells.

In one aspect, the present invention relates to the use of extract from rabbit skin inflamed by vaccinia virus in the preparation of a medicament for eliminating or reducing bone marrow suppression in a patient receiving anti-cancer therapy. In one aspect, the present invention relates to extract from rabbit skin inflamed by vaccinia virus for use in eliminating or reducing bone marrow suppression in a patient receiving anti-cancer therapy. In one aspect, the present invention relates to a method for eliminating or reducing bone marrow suppression in a patient receiving anti-cancer therapy, the method comprising administering a therapeutically effective amount of extract from rabbit skin inflamed by vaccinia virus to the patient receiving anti-cancer therapy. In this aspect, eliminating or reducing bone marrow suppression comprises increasing the number of white blood cells.

In one aspect, the present invention relates to the use of extract from rabbit skin inflamed by vaccinia virus in the preparation of a medicament for preventing or treating pancytopenia induced by anti-cancer therapy in a patient. In one aspect, the present invention relates to extract from rabbit skin inflamed by vaccinia virus for use in the prevention or treatment of pancytopenia induced by anti-cancer therapy in a patient. In one aspect, the present invention relates to a method of preventing or treating pancytopenia induced by anti-cancer therapy in a patient, the method comprising administering a therapeutically effective amount of extract from rabbit skin inflamed by vaccinia virus to the patient. In the aspect, the pancytopenia includes leukopenia.

In one aspect, the present invention relates to the use of extract from rabbit skin inflamed by vaccinia virus in the preparation of a medicament for restoring or increasing whole blood cells in a patient receiving anti-cancer therapy. In one aspect, the present invention relates to extract from rabbit skin inflamed by vaccinia virus for use in restoring or increasing whole blood cells in a patient receiving anti-cancer therapy. In one aspect, the present invention relates to a method for restoring or increasing whole blood cells in a patient receiving anti-cancer therapy, the method comprising administering a therapeutically effective amount of extract from rabbit skin inflamed by vaccinia virus to the patient. In one aspect, the whole blood cells are white blood cells.

In one aspect, the present invention relates to the use of extract from rabbit skin inflamed by vaccinia virus in the preparation of a medicament for preventing, alleviating or treating weight loss induced by anti-cancer therapy in a patient. In one aspect, the present invention relates to extract from rabbit skin inflamed by vaccinia virus for use in the prevention, alleviation or treatment of weight loss induced by anti-cancer therapy in a patient. In one aspect, the present invention relates to a method for alleviating or treating weight loss induced by anti-cancer therapy in a patient, the method comprising administering a therapeutically effective amount of extract from rabbit skin inflamed by vaccinia virus to the patient. In the aspect, the patient is a patient receiving anti-cancer therapy. In the aspect, extract from rabbit skin inflamed by vaccinia virus are used to increase the weight of a patient receiving anti-cancer therapy. It is worth emphasizing that the weight recovery or gain of a patient receiving antibody therapy can be an indicator of the recovery of hematopoietic function or alleviation of bone marrow suppression in the patient, and therefore can further reflect the therapeutic effect of the extract of the present invention.

In one aspect, the present invention relates to a pharmaceutical composition comprising extract from rabbit skin inflamed by vaccinia virus and optionally a pharmaceutically acceptable carrier, adjuvant or excipient. In one aspect of the present invention, the pharmaceutically acceptable carrier, adjuvant or excipient are those that formulate the drug into an oral formulation or an injection. In one aspect, the extract from rabbit skin inflamed by vaccinia virus is formulated into an oral formulation or an injection, preferably an intramuscular injection or an intravenous injection. In one aspect, the extract from rabbit skin inflamed by vaccinia virus is Lepalvir.

In one aspect of the present invention, the anti-cancer therapy includes anti-cancer radiotherapy or anti-cancer drug therapy. In one aspect of the present invention, the anti-cancer therapy comprises administering a cytotoxic drug to a patient. In one aspect of the present invention, the anti-cancer drugs include drugs that directly act on DNA. In one aspect of the present invention, the anti-cancer drugs include alkylating agents, more preferably nitrogen mustards, such as cyclophosphamide. The dosage and administration regimen of anti-cancer therapy can be selected by those skilled in the art according to the actual situation; consequently they are not conditions that limit the implementation of the present invention.

In one aspect of the present invention, the extract from rabbit skin inflamed by vaccinia virus (preferably Lepalvir) is administered to a patient, preferably human in an amount of about 0.01 to about 5 U/kg, preferably about 0.1 to about 2.5 U/kg, more preferably about 0.15 to about 1.15 U/kg. For example, the extract from rabbit skin inflamed by vaccinia virus is administered to a patient, preferably human in an amount selected from the following: about 0.01 U/kg, about 0.02 U/kg, about 0.05 U/kg, about 0.1 U/kg, about 0.15 U/kg, about 0.2 U/kg, about 0.25 U/kg, about 0.3 U/kg, about 0.35 U/kg, about 0.5 U/kg, about 0.6 U/kg, about 0.8 U/kg, about 1 U/kg, about 1.05 U/kg, about 1.1 U/kg, about 1.13 U/kg, about 1.14 U/kg, about 1.15 U/kg, about 1.17 U/kg, about 1.18 U/kg, about 1.2 U/kg, about 1.3 U/kg, about 1.4 U/kg, about 1.5 U/kg, about 1.8 U/kg, about 2 U/kg, about 2.5 U/kg, about 3.5 U/kg, about 4.5 U/kg and the ranges bounded by these numbers. It is known to those skilled in the art that for the dosage, human dose (U/kg or mg/kg)=mouse dose (U/kg or mg/kg)/12.3; or human dose (U/kg or mg/kg)=mouse dose (U/kg or mg/kg)×0.08. The above dosage can be an effective amount for treating the above-mentioned diseases in a patient. In one aspect, the extract from rabbit skin inflamed by vaccinia virus is administered by injection at the above-mentioned dose, such as intramuscular injection or intravenous injection.

In one aspect of the present invention, the prepared medicament contains about 0.6 to about 600 U, preferably about 6 to about 300 U, more preferably about 9 to about 70 U of extract from rabbit skin inflamed by vaccinia virus. The medicament is used for administration to human, such as an adult. The average weight of an adult is, for example, 60 kg. Accordingly, the amount of the extract from rabbit skin inflamed by vaccinia virus contained in the medicament prepared by the present invention is, for example, about 0.6 U, about 1.2 U, About 3 U, about 3.5 U, about 3.6 U, about 6 U, about 9 U, about 12 U, about 15 U, about 18 U, about 21 U, about 30 U, about 36 U, about 40 U, about 60 U, about 63 U, about 66 U, about 67.8 U, about 68.4 U, about 69 U, about 69.5 U, about 70 U, about 70.2 U, about 70.8 U, about 72 U, about 78 U, about 84 U, about 90 U, about 108 U, about 120 U, about 150 U, about 210 U, about 270 U, and the ranges bounded by these numbers. In one aspect, the medicament is prepared as an injection, such as an intramuscular injection or an intravenous injection. In one aspect, the medicament or injection is a fixed dose that cannot be divided. In one aspect, the medicament or injection cannot be divided into smaller doses within 1, 2, 3, 4, 5, 6 or 7 days. In one aspect, the medicament or injection is administered only once within 1, 2, 3, 4, 5, 6 or 7 days.

In one aspect of the present invention, the extract from rabbit skin inflamed by vaccinia virus can be administered simultaneously, separately or sequentially with anti-cancer therapy. In one aspect, the extract can be administered before or after anti-cancer therapy. In one aspect, the extract from rabbit skin inflamed by vaccinia virus is administered to a patient about 1-7 days, preferably 1-6 days, such as within 1, 2, 3, 4, or 5 days after the anti-cancer therapy is given to the patient. In one aspect, the extract from rabbit skin inflamed by vaccinia virus is administered to a patient about 1 to about 72 hours, preferably about 2 to about 48 hours, more preferably about 3 to about 24 hours, more preferably about 5 to about 12 hours, more preferably about 6 to about 8 hours, more preferably about 6 hours after the anti-cancer therapy is given to the patient. In one aspect of the present invention, the extract from rabbit skin inflamed by vaccinia virus is administered to a patient every about 6 to about 72 hours, preferably about 12 to about 60 hours, more preferably about 24 to about 48 hours, more preferably about 36 to about 48 hours, more preferably about 48 hours. In one aspect of the present invention, the duration of administration of the extract to a patient receiving anti-cancer therapy is at least about 24 months, at least about 12 months, at least about 6 months, at least about 2 months, at least about 1 month, at least about 3 weeks, at least about 2 weeks, at least about 10 days, at least about 7 days, at least about 5 days, or at least about 2 days.

In one aspect, the extract from rabbit skin inflamed by vaccinia virus causes an elevation in white blood cells in a patient after administration for 1-12 days, preferably 2-8 days, more preferably 4-7 days (e.g., 4, 5, 6 or 7 days), in which the level of elevation is higher than that for a patient who did not receive the extract. In this aspect, the patient receiving the extract exhibits a level of leukocyte elevation that is at least about 1 times, at least about 1.01 times, at least about 1.05 times, at least about 1.1 times, at least about 1.2 times, at least about 1.3 times, at least about 1.4 times, at least about 1.5 times, at least about 1.8 times, at least about 2 times, at least about 2.5 times, at least about 5 times, at least about 8 times, at least about 10 times, at least about 20 times, for example about 1.01 to about 2 times higher than the patient who did not receive the extract.

In one aspect of the invention, the patient may be a mammal, preferably a human. In this aspect, the patient is a human patient receiving anti-cancer therapy. In another aspect, the patient is a human patient suffering from hematopoietic system damage or bone marrow suppression induced by anti-cancer therapy. Further, white blood cell reduction or leukopenia in a human patient is induced or caused by the hematopoietic system damage or bone marrow suppression.

As used herein, "extract from rabbit skin inflamed by vaccinia virus" and "extract from rabbit skin inflamed by vaccinia vaccine" can be used interchangeably, and refers to an extract, which contains active substances and is extracted from the inflamed rabbit skin inoculated with vaccinia virus using such processes as leaching, purification, and refining. This extract is usually a yellow or light yellow liquid, but it can also be dried into a solid. The injection of this extract from rabbit skin inflamed by vaccinia virus is commercially available under the trade name Lepalvir, produced by Vanworld Pharmaceutical (Rugao) Co. Ltd. In one aspect, the preparation method of extract from rabbit skin inflamed by vaccinia virus or Lepalvir is described in Chinese Patent Publication Nos. CN1205233A, CN1613305A and CN1493302A, PCT Publication No. WO2004/060381, and European Patent Publication No. EP1557171, etc., the entirety of which is incorporated herein by reference.

In one aspect, the extract from rabbit skin inflamed by vaccinia virus or Lepalvir can be prepared by a method including the following steps:

(1) The inflamed rabbit skin after inoculation with vaccinia virus is collected, fragmented, and extracted with an extraction solvent to obtain solution A;
(2) Solution A is treated with acid and heat to obtain solution B;
(3) Solution B is treated with alkali and heat to obtain solution C;
(4) Solution C is subject to adsorption and filtration under acidic conditions, and desorption under alkaline conditions to obtain solution D;
(5) Solution D is neutralized and heated to obtain solution E;
(6) Solution E is concentrated to obtain the extract; and
(7) Optionally the extract is mixed with pharmaceutically acceptable carrier, adjuvant or excipient.

In one aspect, in step (1), the rabbit is inoculated with vaccinia virus; the skin with pox is collected; the skin is fragmented; an aqueous solution of phenol is added, and the skin is soaked at a temperature of lower than about 12° C. (for example, about 0-10° C., preferably about 2-8° C., more preferably about 3-6° C., more preferably about 4° C.) for at least about 12 hours (for example, about 24-90 hours, preferably about 48-72 hours, more preferably about 70 or about 72 hours). The supernatant is obtained by centrifugation, and solution A is obtained by filtration. The phenol concentration in the phenol aqueous solution is about 1%-10%, preferably about 2%-5%, more preferably about 2% or about 3%.

In one aspect, in step (2), the solution A is adjusted to acidic (for example, about pH 4-6, more preferably about pH 4.5-5.5, more preferably about pH 5) with acid (for example, hydrochloric acid), and heated (for example, at about 90-100° C., preferably about 95° C. for at least about 10 minutes, such as about 20-50 minutes, preferably about 30-40 minutes), optionally lowering the temperature (for example, to less than about 50° C., preferably less than about 30° C.), followed by centrifugation to obtain the supernatant, and filtration to obtain solution B. The step (2) can be performed in a nitrogen environment.

In one aspect, in step (3), the solution B is adjusted to alkaline (e.g., about pH 8-10, more preferably about pH 8.5-9.5, more preferably about pH 9 or about pH 9.2), and heated (for example, at about 90-100° C., preferably about 95° C. for at least 10 minutes, such as about 30-50 minutes, preferably about 30-40 minutes), optionally lowering the temperature (for example, to less than about 50° C., preferably less than about 30° C.), followed by filtration to obtain solution C. The step (3) can be performed in a nitrogen environment.

In one aspect, in step (4), the solution C is adjusted to acidic (for example, about pH 3-6, more preferably about pH 4-5, more preferably about pH 4.5) with an acid (for example, hydrochloric acid), and an adsorbent is added thereto (For example, activated carbon) for soaking (for example, under stirring for at least about 1 hour, preferably about 2-10 hours, more preferably about 4 hours), after which the solution is removed and the adsorbent containing the active ingredient is collected. Subsequently, the above-mentioned adsorbent is added to the eluent (for example, water), and the pH is adjusted to alkaline (for example, about pH 9-12, preferably about pH 10 or pH 11) with a base (for example, sodium hydroxide) to separate the active ingredient from the adsorbent (for example, stirring for at least about 1 hour, preferably 2-10 hours, more preferably 4 hours, followed by filtration, and then washing the adsorbent with water) to obtain solution D. The step (4) can be performed in a nitrogen environment.

In one aspect, in step (5), solution D is adjusted to weakly acidic (for example, about pH 5.5-6.6, preferably about pH 6) with acid (for example, hydrochloric acid) to obtain solution E. Preferably, the step (5) can be performed under aseptic conditions.

In one aspect, in step (6), the solution E is concentrated (for example, concentrated under reduced pressure, preferably concentrated by evaporation under reduced pressure, for example, at about 50° C. to 70° C., preferably at about 54° C. to 56° C.), followed by filtration to obtain an extract containing the active ingredient. The step (6) can be performed in a nitrogen environment.

As used herein, "anti-cancer therapy", "anti-tumor therapy", "cancer therapy", and "tumor therapy" can be used interchangeably, and may refer to a treatment method implemented on a patient's cancer or tumor. The anti-cancer therapy includes drug therapy and radiation therapy, wherein the drug therapy includes chemotherapy. These treatments can cause side effects on patient, including impairment of hematopoietic function such as bone marrow suppression, gastrointestinal reactions such as nausea and vomiting, toxicity such as cardiotoxicity and respiratory system toxicity, and hair loss.

As used herein, "anti-cancer drug therapy", "anti-cancer agent", and "anti-tumor agent" can be used interchangeably and refer to drug treatment implemented on a patient's cancer or tumor. "Anti-cancer agent" may include cytotoxic agents and non-cytotoxic agents, and the cytotoxic agents may include agents that directly act on nucleic acids (such as DNA or RNA), antimetabolites (such as agents that interfere with DNA synthesis), and agents that act on structural protein, etc. In one aspect, the anti-cancer agent may include an alkylating agent, and the alkylating agent may include nitrogen mustards. Cyclophosphamide belongs to the nitrogen mustard anti-cancer agent.

As used herein, "hematopoietic system" is usually composed of two parts: hematopoietic organs and hematopoietic cells. It is the whole system for producing blood in the body, mainly including yolk sac, liver, spleen, kidney, thymus, lymph node and bone marrow. In the present invention, the hematopoietic system damaged by anti-cancer therapy may involve bone marrow, liver, spleen and lymph node, preferably bone marrow.

As used herein, "bone marrow suppression" and "bone marrow function suppression" can be used interchangeably, and can include a decrease in the activity or number of blood cell precursors in the bone marrow, for example, caused by anti-cancer therapy. Blood cells in the bloodstream have a short lifespan and often require constant replenishment. In order to achieve the purpose of timely replenishment, stem cells, which are precursors of blood cells, must divide rapidly. Drug therapy (such as cyclophosphamide) and radiation therapy, as well as many other anti-tumor treatments, are targeted at rapidly dividing cells, which often results in the suppression of normal bone marrow cells. In the bone marrow suppression caused by most anti-cancer therapies, dominantly white blood cells usually decline rapidly. Therefore, the number of white blood cells can be detected after chemotherapy to determine whether bone marrow suppression occurs, and the effect of the drug on the recovery of white blood cells is therefore also an important indicator of the efficacy of the drug in the treatment of bone marrow suppression.

As used herein, "leukopenia" typically refers to a symptom when the number of white blood cells in the peripheral blood continues to fall below $4 \times 10^9$/liter. Anti-cancer therapy not only kills tumor cells, but also causes severe damage to normal cells, especially proliferating cells such as bone marrow hematopoietic cells, resulting in a decline in blood cells. Clinically, severe infections and the like often secondary to leukopenia affect the smooth progress of cancer therapy, resulting in a decrease in clinical efficacy and a decline in the life quality of the patient. Therefore, raising peripheral blood leukocytes in anti-cancer therapy has become the key to ensuring the completion of anti-cancer therapy and improving the effect of anti-cancer therapy.

As used herein, "pancytopenia" may refer to a medical symptom of a decrease in the number of red blood cells, white blood cells, and platelets in the blood, which may include a decrease in blood cells caused by damage to hematopoietic function or suppression of bone marrow function. In cancer therapy, the reduction of blood cells is mainly manifested as the reduction of white blood cells and is more apparent. Therefore, the effect of drugs on increasing white blood cells can reasonably reflect its effect on pancytopenia.

The side effects of anti-cancer therapy can cause weight loss in a patient. Therefore, the effect of the drug on the weight gain of the patient can also be an indicator of its effective reduction or treatment of the side effects (such as hematopoietic system damage, bone marrow suppression, pancytopenia, leukopenia, etc.).

DETAILED DESCRIPTION

Figure 1:
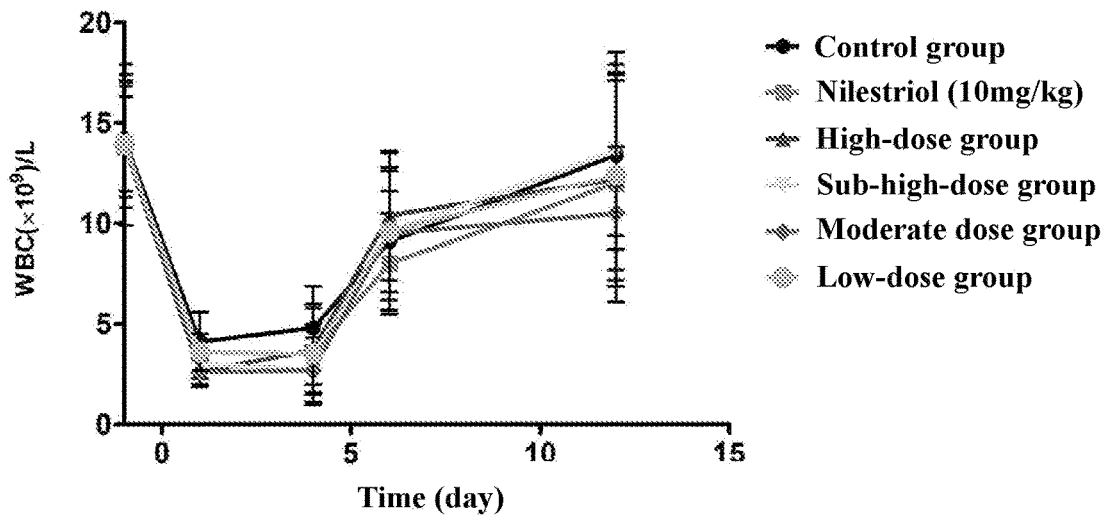
FIG. 1. The change curve of the effect of Lepalvir on the peripheral blood WBC in mice exposed to cyclophosphamide (250 mg/kg). WBC: White blood cells.

Unless otherwise specified, all scientific terms used herein have the same meaning as commonly understood by those of ordinary skill in the art. Exemplary methods and materials are described below, and equivalents can be used. All publications and other references mentioned herein are incorporated by reference in their entirety.

The following examples are provided to further illustrate the present invention. The following examples are not intended to limit the scope of the present invention for any reason.

EXAMPLES

Example 1—Protective Effect of Lepalvir on Hematopoietic System Damage Caused by Cytotoxic Drug 1. Test Purpose Using the hematopoietic system damage model in which the mouse has been exposed to cyclophosphamide, the effect of Lepalvir on the peripheral blood WBC of model mouse is observed, and whether Lepalvir has the effect of promoting hematopoietic function in mice is examined.

2. Experimental Material 2.1 Test Drug

Lepalvir, provided by Vanworld Pharmaceutical (Rugao) Co. Ltd.

2.2 Positive Control Drug

Nilestriol, provided by Room 9, Institute of Radiation Medicine, Academy of Military Medical Sciences.

2.3 Experimental Animal

Adult KM mice were bred in the Experimental Animal Center of the Academy of Military Medical Sciences. The weight of the mouse was 18.0-20.0 g. Laboratory animal license number: SCXK-(Military) 2002-001. The experimental animals were raised in the animal laboratory of the Academy of Military Medical Sciences. Laboratory certificate number: SYXK (Military)-2002-016. There were 10 mice in each cage, fed with feed specially formulated for mouse, and free drinking water. The temperature in the animal laboratory was maintained at about 25° C., the relative humidity was maintained at 40-70%, with the daily light of 12 hours.

3. Experimental Method 3.1 Grouping Method

There were six groups in the experiment: model control group, positive drug control group (nilestriol 10 mg/kg), Lepalvir high-dose group (14.4 U/kg), Lepalvir sub-high-dose group (7.2 U/kg), Lepalvir moderate dose group (3.6 U/kg), and Lepalvir low dose group (1.8 U/kg). Mice were randomly grouped according to the average number of normal blood WBC before the two administrations, with 10 mice in each group.

3.2 Modeling Method

The mouse was given cyclophosphamide (250 mg/kg) at a time with a volume of 200 µl, and the route of administration was intraperitoneal injection.

3.3 Method of Administration

The positive drug nilestriol (10 mg/kg) was given once 6 hours after the administration of cyclophosphamide with a volume of 200 µl. Administration for each Lepalviri group began 6 hours after the dosing of cyclophosphamide. Lepalviri was administered once every 48 hours for two consecutive weeks, and the mode of administration was intramuscular injection.

3.4 Drug Efficacy Test Indicators in the Mouse

The normal blood indicators of the mouse before modeling were examined, and the WBC indicators were examined every 2-3 days after the dosing of cyclophosphamide, until the blood was completely restored. At the end of the execution of the mouse, the bone marrow specimens were preserved in formalin to prepare bone marrow slices to observe the changes in bone marrow tissue.

3.5 Data Processing

The measurement data was expressed as $\bar{x}\pm s$, and the statistical analysis between the groups was performed using the t-test program in the EXCEL software. GraphPad Prism5 was employed to prepare the change curve of various types of WBC indicators.

4. Experimental Results 4.1 Effect on Mouse WBC

The number of WBC decreased to the lowest value one day after cyclophosphamide exposure, and then began to rise, and the recovery rate of the Lepalvir administration group was faster compared with the model control group. Each group recovered to close to the pre-dose normal value at day 12. See Table 1 and FIG. 1 for details.

TABLE 1

The effect of Lepalviri on the peripheral blood WBC in the mouse exposed to cyclophosphamide (250 mg/kg)

| Group | $WBC/\times 10^{12} \cdot L^{-1}$ | | | | |
| --- | --- | --- | --- | --- | --- |
| | normal | 1 d after modeling | 4 d after modeling | 6 d after modeling | 12 d after modeling |
| Model control group | 14.2 ± 2.9 | 4.1 ± 1.5 | 4.8 ± 2.1 | 9.1 ± 2.5 | 13.4 ± 4.0 |
| Nilestriol 10 mg/kg | 13.8 ± 2.5 | 3.6 ± 0.9 | 3.5 ± 2.5 | 8.0 ± 2.5 | 12.0 ± 5.9 |
| Lepalvir high-dose group | 14.2 ± 2.6 | 2.6 ± 0.7* | 3.7 ± 2.1 | 10.4 ± 3.2 | 12.2 ± 5.3 |
| Lepalvir sub-high-dose group | 14.1 ± 3.3 | 3.0 ± 0.7* | 2.7 ± 1.2* | 9.6 ± 3.0 | 13.6 ± 4.9 |

TABLE 1-continued

The effect of Lepalviri on the peripheral blood WBC
in the mouse exposed to cyclophosphamide (250 mg/kg)

| | WBC/×10$^{12}$ · L$^{-1}$ | | | | |
|---|---|---|---|---|---|
| Group | normal | 1 d after modeling | 4 d after modeling | 6 d after modeling | 12 d after modeling |
| Lepalvir moderate dose group | 13.9 ± 3.1 | 2.6 ± 0.6* | 2.7 ± 1.6* | 9.5 ± 3.3 | 10.5 ± 3.3 |
| Lepalvir low-dose group | 13.9 ± 4.0 | 3.6 ± 0.9 | 3.5 ± 1.5 | 9.6 ± 3.9 | 12.4 ± 4.7 | vs: model control,
*P < 0.05,
"**" P < 0.01,
"***" P < 0.001

5. Evaluation

During the observation period, the WBC counts in the peripheral blood of the animal changed significantly. One day after the administration of cyclophosphamide, the WBC concentration in the model control group dropped to the lowest level, and then slowly recovered, and it was close to the pre-dose measurement value 12 days after the model was generated.

Figure 2:
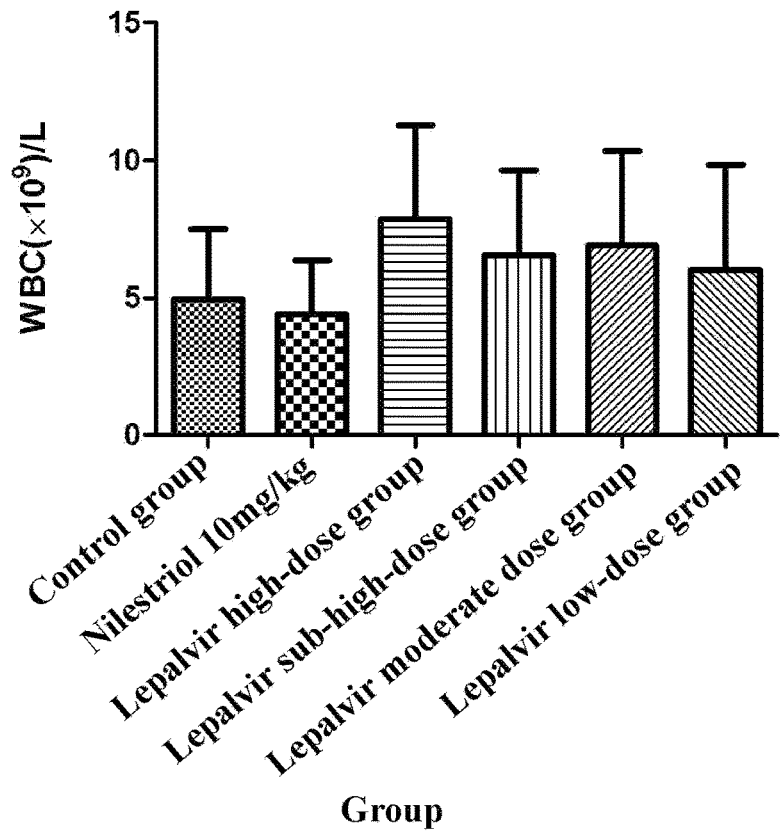
FIG. 2. The effect of Lepalvir on the increase in the concentration of peripheral blood WBC in mice exposed to cyclophosphamide (day 6). WBC: White blood cells.

The dosing started 6 hours after the administration of cyclophosphamide. As shown in Table 1 and FIG. 1, on the 6$^{th}$ day after modeling, the WBC concentration of the test drug group increased higher than that of the control group, suggesting that the test drug had a promoting effect during the recovery phase of the hematopoietic system. FIG. 2 more directly shows the effect of Lepalvir on promoting the recovery of the hematopoietic system.

6. Conclusion

It was suggested that at the hematopoietic recovery stage, the tested drug effectively promoted the recovery of WBC indicators in the mouse. This further rationally indicated that Lepalvir is capable of effectively treating hematopoietic system damage and bone marrow suppression induced by anti-cancer therapy.

Example 2—Effect of Lepalvir on Cytotoxic Drug-Induced Weight Loss

1. Test Purpose

Using the bone marrow injury model in which the mouse has been exposed to cyclophosphamide, the effect of the tested drug on the body weight of the model mouse is observed.

2. Experimental Material 2.1 Test Drug

Lepalvir, provided by Vanworld Pharmaceutical (Rugao) Co. Ltd.

2.2 Cyclophosphamide for Injection

Cyclophosphamide, provided by Jiangsu Shengdi Pharmaceutical Co., Ltd.

2.3 Experimental Animal

Adult KM mice, Beijing Vital River Laboratory Animal Technology Co., Ltd. The weight of the mouse was 18.0-22.0 g, female. Laboratory animal license number: SCXK—(Beijing) 2016-0011 (NO. 11400700269430). The experimental animals were raised in the animal laboratory of the Academy of Military Medical Sciences, and the facility use permit was SYXK (Military) 2012-0021. There were 10 mice in each cage, fed with feed specially formulated for mouse, and free drinking water. The temperature in the animal laboratory was maintained at about 25° C., the relative humidity was maintained at 40-70%, with the daily light of 12 hours.

3. Experimental Method 3.1 Model Establishment

A blank control group of 7 mice was divided from the KM mice according to their body weight.

The remaining KM mice were used for intraperitoneal injection of cyclophosphamide (300 mg/kg) to establish the model. 3 days after the model establishment, the blood of the model KM mouse was examined. Mice were randomly grouped according to the blood WBC count of the KM mouse, with 10 animals in each group.

3.2 Grouping Method

Grouping and treatment methods are as follows:

1) Blank control group, 7 mice;

2) Model control group, 10 mice;

3) Lepalvir high-dose group, intravenous injection, dose 14.4 U/kg, 10 mice;

4) Lepalvir low-dose group, intravenous injection, dose 1.8 U/kg, 10 mice.

3.3 Method of Administration

Dosing for each test drug group started on the second day after grouping (4 days after the model establishment), and the drug was given once every 48 hours for a total of 4 times.

3.4 Weight Measurement

The body weight of KM mouse was measured on the 3$^{rd}$ day (−3 d) before administration and 1, 3, 5, 8 and 10 days after administration (1 d, 3 d, 5 d, 8 d and 10 d).

3.5 Statistical Method

The measurement data was represented by X±S, and the Student's t test was used for statistical analysis.

4. Results of Drug Efficacy Test

The body weight of the experimental animals in each group of the model was decreased, which was significantly lower than that of the blank control group (P<0.05). The weight gradually recovered from the 5$^{th}$ day of treatment, and the weight recovered significantly from the 8$^{th}$ day of treatment, which was significantly different from the model control group (P<0.05). See Tables 2 and 3.

TABLE 2

Changes in body weight of the KM model mouse and the mouse in each treatment group

| Group | weight (g) | | | | | |
|---|---|---|---|---|---|---|
| | −3 d | 1 d | 3 d | 5 d | 8 d | 10 d |
| Normal control | 23.24 ± 0.52 | 25.87 ± 1.42 | 26.76 ± 1.76 | 26.66 ± 1.81 | 28.54 ± 1.94 | 29.26 ± 1.83 |
| Model control | 23.02 ± 0.62 | 22.02 ± 0.99*** | 21.83 ± 0.93*** | 22.55 ± 0.95*** | 23.66 ± 1.08*** | 24.68 ± 1.02*** |
| Lepalvir low 1.8 U/kg | 22.93 ± 0.51 | 22.12 ± 0.97*** | 22.04 ± 1.53*** | 23.30 ± 1.31*** | 25.94 ± 1.60**⊕ ⊕ | 26.71 ± 1.51⊕ ⊕ |
| Lepalvir high 14.4 U/kg | 23.12 ± 0.60 | 22.19 ± 0.67*** | 22.42 ± 0.95*** | 23.77 ± 1.30** | 26.17 ± 1.36*⊕ ⊕ ⊕ | 27.20 ± 1.71⊕ ⊕ ⊕ |

Note:
compared with the blank control group, "*" P < 0.05; "" P < 0.01; "*" P < 0.001;
compared with the model control group, "⊕" P < 0.05; "⊕ ⊕" P < 0.01; "⊕ ⊕ ⊕" P < 0.001.

TABLE 3

The relative increase changes in body weight of the KM model mouse and the mouse in each treatment group

| Group | Relative weight | | | | | |
|---|---|---|---|---|---|---|
| | −3 d | 1 d | 3 d | 5 d | 8 d | 10 d |
| Normal control | 1.00 ± 0.00 | 1.11 ± 0.05 | 1.15 ± 0.06 | 1.15 ± 0.06 | 1.23 ± 0.07 | 1.26 ± 0.07 |
| Model control | 1.00 ± 0.00 | 0.96 ± 0.05*** | 0.95 ± 0.05*** | 0.98 ± 0.05*** | 1.03 ± 0.05*** | 1.07 ± 0.06*** |
| Lepalvir low 1.8 U/kg | 1.00 ± 0.00 | 0.97 ± 0.05*** | 0.96 ± 0.07*** | 1.02 ± 0.06*** | 1.13 ± 0.07*⊕ ⊕ | 1.16 ± 0.06*⊕ ⊕ |
| Lepalvir high 14.4 U/kg | 1.00 ± 0.00 | 0.96 ± 0.04*** | 0.97 ± 0.05*** | 1.03 ± 0.06** | 1.13 ± 0.06**⊕ ⊕ ⊕ | 1.18 ± 0.07*⊕ ⊕ |

Note:
compared with the blank control group, "*" P < 0.05; "" P < 0.01; "*" P < 0.001;
compared with the model control group, "⊕" P < 0.05; "⊕ ⊕" P < 0.01; "⊕ ⊕ ⊕" P < 0.001.

5. Test Evaluation

In the mouse bone marrow hematopoietic injury model caused by cyclophosphamide, the weight of the mouse decreased. The test drug had a promoting effect on the weight recovery of mouse, and there was a significant statistical difference compared with the model control group.

6. Conclusion

The test drug Lepalvir can promote the weight recovery of mouse in the bone marrow injury model caused by cyclophosphamide, which indirectly showed that it can effectively alleviate the hematopoietic system damage and bone marrow suppression caused by anti-cancer treatment.

The invention claimed is:

1. A method of treating leukopenia induced by anti-cancer therapy in a patient in need thereof, wherein the method comprises administering to the patient a composition comprising a therapeutically effective amount of an extract from rabbit skin inflamed by vaccinia virus.

2. The method of claim 1, wherein the anti-cancer therapy comprises anti-cancer radiotherapy or anti-cancer drug therapy;
wherein the anti-cancer drug therapy comprises an alkylating agent.

3. The method of claim 1, wherein the composition is administered orally or by injection;
wherein the injection is an intramuscular injection or an intravenous injection.

4. The method of claim 1, wherein the extract from rabbit skin inflamed by vaccinia virus is administered to the patient in an amount of 0.01 U/kg to 5 U/kg, 0.1 U/kg to 2.5 U/kg, or 0.15 U/kg to 1.15 U/kg; or
the composition comprises 0.6 U to 300 U, 6 U to 150 U, or 9 U to 70 U of the extract from rabbit skin inflamed by vaccinia virus.

5. The method of claim 2, wherein the alkylating agent is cyclophosphamide.

6. The method of claim 1, wherein the patient is human.

* * * * *